(12) United States Patent
Sangha et al.

(10) Patent No.: US 8,075,850 B2
(45) Date of Patent: Dec. 13, 2011

(54) TOUCH EVIDENCE COLLECTION APPARATUS AND METHOD

(75) Inventors: Jangbir S. Sangha, Overland Park, KS (US); Todd Bille, Annandale, VA (US)

(73) Assignee: The Bode Technology Group, Inc., Lorton, VA (US)

( * ) Notice: Subject to any disclaimer, the term of this patent is extended or adjusted under 35 U.S.C. 154(b) by 1253 days.

(21) Appl. No.: 11/653,116

(22) Filed: Jan. 12, 2007

(65) Prior Publication Data
US 2007/0166198 A1  Jul. 19, 2007

Related U.S. Application Data

(60) Provisional application No. 60/758,855, filed on Jan. 13, 2006.

(51) Int. Cl.
*G01N 31/22* (2006.01)
*G01N 33/49* (2006.01)
*G01N 33/493* (2006.01)

(52) U.S. Cl. ........ 422/406; 422/411; 401/118; 401/126; 401/129; 435/288.1; 435/810

(58) Field of Classification Search .................. 422/406, 422/411; 401/118, 126, 129; 435/288.1, 435/810; 600/572, 573; 604/1
See application file for complete search history.

(56) References Cited

U.S. PATENT DOCUMENTS 6,174,099 B1 * 1/2001 Patel et al. .................. 401/129
2005/0252820 A1 * 11/2005 Sanchez-Felix et al. ..... 206/569

* cited by examiner

*Primary Examiner* — In Suk Bullock
*Assistant Examiner* — Paul Hyun
(74) *Attorney, Agent, or Firm* — Polsinelli Shughart P.C.; Richard Stitt

(57) ABSTRACT

A specimen collection apparatus and method is provided that allows for obtaining a specimen of evidence from a crime scene or evidence of any event and the sequential use and transfer and analysis of such evidence in a manner which maintains a demonstrable chain of custody.

4 Claims, 8 Drawing Sheets

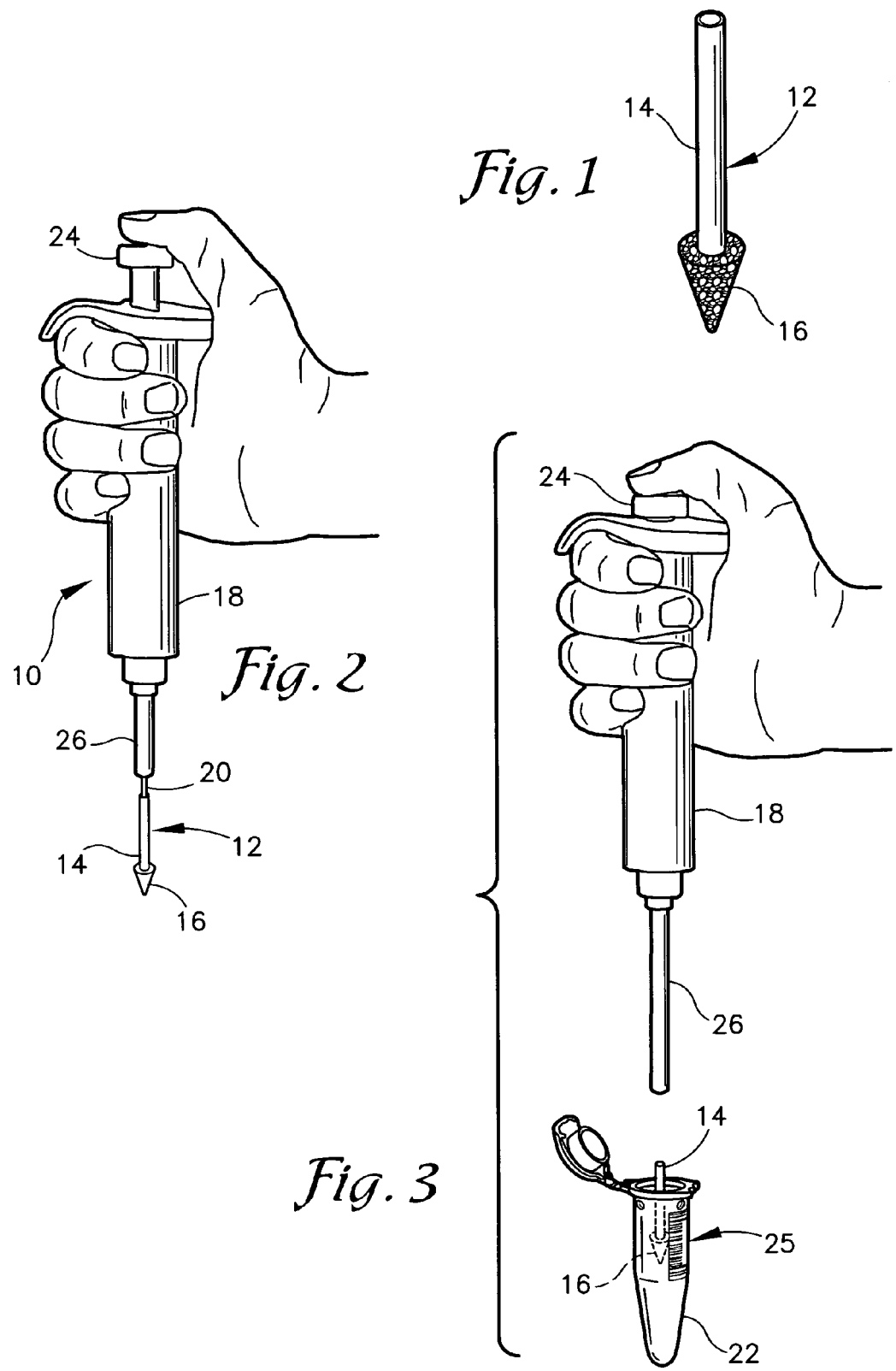

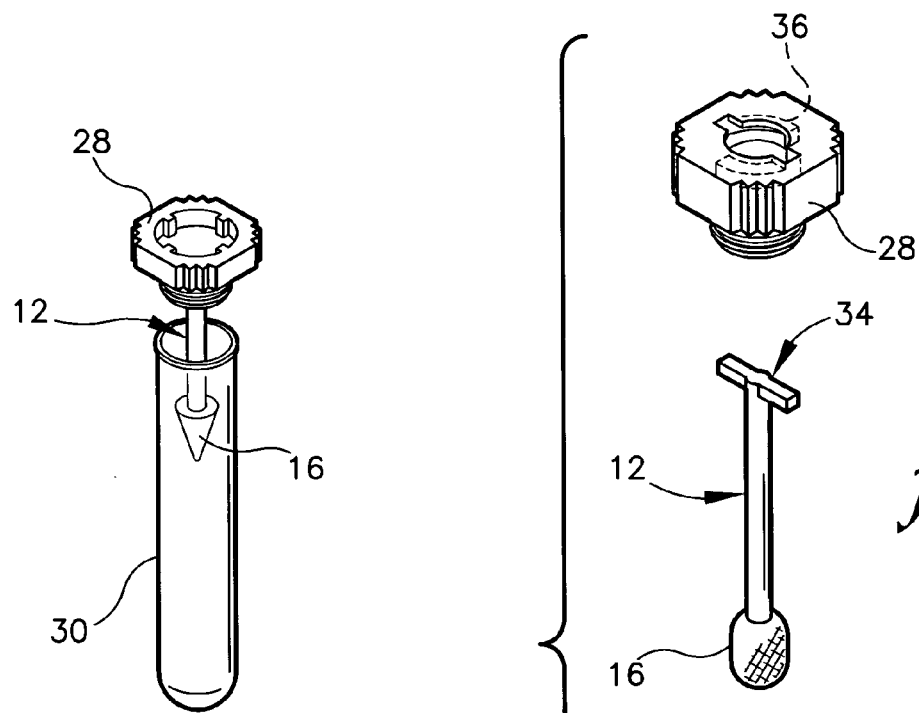
Fig. 4
Fig. 5
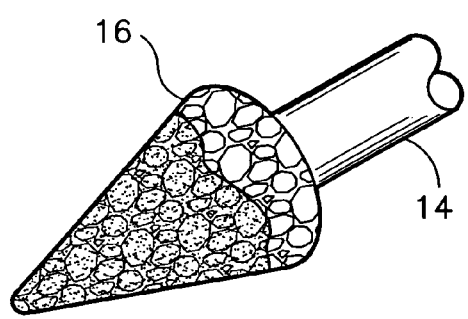
Fig. 6

TOUCH EVIDENCE COLLECTION APPARATUS AND METHOD

CROSS-REFERENCE TO RELATED APPLICATION

This application claims priority under 35 U.S.C. 119(e) and 37 C.F.R. 1.78(a)(4) based upon copending U.S. Provisional Application Ser. No. 60/785,855 for TOUCH EVIDENCE COLLECTION APPARATUS AND METHOD, filed Jan. 13, 2006, which is incorporated herein by reference.

FIELD OF THE INVENTION

The present invention is directed to an apparatus and method for collection and transport of touch evidence samples and the method of preparing such evidence or samples for forensic analysis. In particular embodiments of devices for collection of "touch evidence" are provided and methods of extracting such "touch evidence" from the collection device prior to laboratory analysis of the "touch evidence."

BACKGROUND OF THE INVENTION

The present invention relates to an apparatus and method for collecting what is known as "touch evidence" related to any type of situation in which evidence collection is required. Such evidence collection can be associated with crime scenes or can simply be the collection of a DNA sample from a human being in the course of a traffic stop or a paternity investigation. Touch evidence, in general, is that evidence which is located on a surface or on a human being and which can be physically contacted by an evidence collection device to thereby obtain a sample of the evidence. Examples of such touch evidence might be any type of biological fluid, either wet or dried, such as blood, urine or saliva, or any unknown substance which is visible or invisible and which can be located allowing for collection of a specimen of the evidence and capture of such a sample on a touch evidence collector of the type described hereinafter. As previously mentioned, it will be appreciated that such touch evidence collection devices are widely used in criminal investigations, but also are used increasingly in traffic stop situations or traffic arrest situations in which it is desirable to obtain a DNA sample from the suspect as part of a criminal records database requirement.

DESCRIPTION OF THE DRAWINGS

FIG. 1 shows a perspective view of one embodiment of the absorbent collector head.

FIG. 2 shows a perspective view of an embodiment of a handle and an absorbent collector head.

FIG. 3 shows a perspective view showing an absorbent collector head ejected from the handle and into a storage vial.

FIG. 4 shows a perspective view of an embodiment of an evidence collection and storage device.

FIG. 5 shows an exploded view of an embodiment of an evidence collection and storage device.

FIG. 6 shows an enlarged perspective view of an absorbent collector head partially coated in evidence.

DESCRIPTION OF A PREFERRED EMBODIMENT

Figure 7:
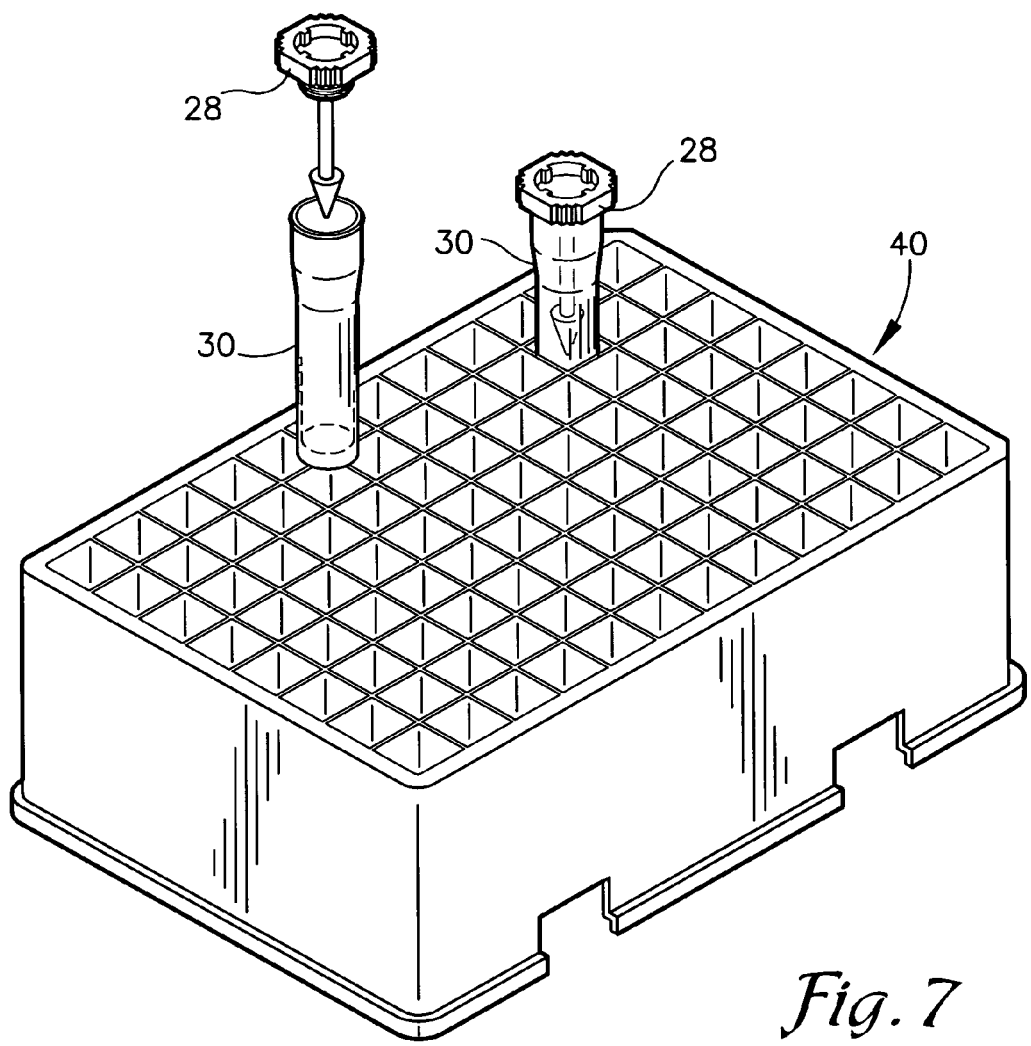
FIG. 7 shows a left side front and top perspective view of a typical assay holder box containing an embodiment of an evidence collection and storage device.

First referring to FIGS. 1-7, an apparatus for a collection of touch evidence and a method of preparing the touch evidence collector for analysis will be described. Referring now to FIGS. 1-3, an evidence collecting device 10 is shown in FIG. 2 which is designed for receiving a generally absorbent collector head 12 shown in FIG. 1. The device 10 shown in FIG. 2 is essentially a handle that is used for manipulating the absorbent collector head 12 of FIG. 1, however, the handle is also provided with an ejector mechanism which allows collector head 12 of FIG. 1 to be ejected from the handle as is shown accomplished in FIG. 3. Now referring particularly to FIG. 1, collector head 12 is comprised of two portions, a shaft portion 14 having an absorbent collector 16 mounted on the end of shaft 14. Shaft 14 can either be a hollow tube or a solid tube depending on the configuration of handle 18 (FIG. 2). The particular structure of collector head 12 and its manner of attachment to handle 18 will be understood by those skilled in the art and the particular construction of collector head 12 and handle 18 to allow the securing of collector head 12 onto handle 18 while allowing for ejection of absorbent collection head 16 from shaft 14 at the end of collecting a sample on absorbent collector 16 will be readily apparent to those skilled in the art.

Referring now to FIG. 2, in preparation for acquiring a touch sample or touch sample evidence, collector head 12 is mounted onto handle 18 such that shaft 14 of collector head 12 is attached to handle 18. This orientation leaves absorbent collector 16 available for collection of the touch evidence. Once collector head 12 is mounted onto handle 18, the user can use the evidence collecting device 10 (FIG. 2) to manipulate absorbent collector 16 and to place absorbent collector 16 in contact with the touch evidence for which collection is desired. It will be appreciated that handle 18 allows the user to dip absorbent collector 16 into a fluid pool or to rub absorbent collector 16 against a solid, or dried specimen to allow collection of the specimen onto absorbent collector 16. Still referring to FIG. 2, the connection of collector head 12 to handle 18 is essentially achieved by inserting shaft or tube 14 onto a mounting rod 20 which extends from handle 18. Shaft 14 may be manually mounted onto mounting rod 20 either directly by the hand of the user or by grasping collector head 12 with an instrument or a rubber glove to avoid contamination of the entirety of collector head 12. Alternatively, it will be appreciated that a group of collector heads 12 may be provided for use in a pre-packaged stand which exposes shaft 14 but conceals absorbent collector 16 thereby avoiding contamination of absorbent collector 16 as shaft 14 is inserted onto mounting rod 20. Such forms of packaging to facilitate the introduction of collector head 12 onto mounting rod 20 will be apparent to those skilled in the art. Once collector head 12 is mounted onto rod 20, handle 18 is equipped for use in collecting a specimen. At the conclusion of collecting the specimen, it is then desirable to separate absorbent collector 16 from shaft 14 and such separation is facilitated by the construction of handle 18.

Referring now to FIG. 3, the ejection of absorbent collector 16 from shaft 14 is shown. In FIG. 3, collector head 12 and absorbent collector 16 are shown being ejected into vial 22. Vial 22 is a typical one or two milliliter vial that may be used to receive a absorbent for extraction of the specimen therefrom. As shown in FIG. 3, the ejection of collector head 12 and absorbent collector 16 is accomplished by the user depressing plunger 24 of handle 18. The depressing of plunger 24 serves to move ejector 26 downwardly over mounting rod 20 to contact shaft 14 of collector head 12 to press collector head 12 off of mounting rod 20. It will be appreciated that collector head 12 is press fitted or frictionally fitted onto rod 20, and therefore, may be pressed off of rod 20 by ejector tube 26. It further will be appreciated that there is a general coaxial configuration as between shaft 14 and mounting rod 20 and ejector 26. Specifically, mounting rod 20 is mounted within ejector 26 coaxially, and shaft 14 is mounted coaxially onto mounting rod 20. In the functioning of handle 18, when plunger 24 is depressed downwardly, ejector 26 moves downwardly along mounting rod 20 and coaxially thereto, and ejector 26 moves over shaft 14, and coaxially thereto, until contact with absorbent collector 16 is made, and absorbent collector 16 is then pressed off of shaft 14. Once absorbent collector 16 has been removed from shaft 14 and inserted into vial 22, an extraction of fluid may be added to vial 22, or alternatively, the fluid may have been added to vial 22 prior to the ejection of absorbent collector 16 therein, and extraction of the collected touch evidence specimen from absorbent collector 16 and into the fluid within vial 20 can be accomplished. Alternatively, it may be appreciated that vial 22 may simply be a shipping vial of a convenient size, and it may or may not contain a buffer or preservative to prevent mold or bacterial growth on absorbent collector 16 during transport. In the case in which vial 22 is simply a transport device, vial 22 can be either hand carried to a laboratory or inserted into a mailing or shipping envelope or other structure and sent to a lab for analysis. To permit identification of the specimen contained in absorbent collector 16 after it has been inserted into vial 22 a bar code 25 is provided which can be used to associate vial 22 and absorbent collector 16 with any related identification information regarding the sample or specimen.

Referring now to FIG. 4, an alternate structure is shown in which a collector head 12 is mounted on a vial cap 28 with a vial 30 being provided to initially hold and protect collector head 12 and to subsequently receive collector head 12 after a specimen has been collected on absorbent collector 16 as is shown in FIG. 6.

Still referring to FIG. 4, in operation, it will be appreciated that a user receiving the device of FIG. 4 may simply remove vial cap 28 from vial 30 and use vial cap 28 to hold collector head 12 while absorbent collector 16 is introduced into a specimen for collection. The specimen will adhere to absorbent collector 16. After the specimen is collected on absorbent collector 16 vial cap 28, still having collector head 12 attached thereto, may be reinserted into vial 30 for transport to a laboratory for specimen analysis. It can be appreciated that once vial 30, having cap 28 thereon, reaches the testing laboratory that an extraction fluid 32 (FIG. 5) can be placed into vial 30, vial cap 28 replaced, and the specimen in absorbent collector 16 can be extracted into fluid 32 within vial 30. Such extraction may best take place by vigorously vibrating or shaking vial 30 to wet absorbent collector 16 repeatedly with the extraction solution 32. Absorbent collector 16, when vial cap 28 is inserted into vial 30, would be suspended above extraction fluid 32. This arrangement permits the entirety of vial 30, with cap 28 attached, and having collector head 12 still connected to vial cap 28, to be inserted into a centrifuge, and the liquid portion completely removed from absorbent collector 16 by centrifugal force. It will be appreciated that in such circumstances of centrifuging a sample, it is undesirable to have absorbent collector 16 remain within contact of the extraction fluid 32 as this leads to a certain degree of recapture of the sample for extraction within the structural matrix of whatever material absorbent collector 16 is constructed.

Referring now to FIG. 5, an alternative vial and cap apparatus having an absorbent attached thereto is shown. In the apparatus of FIG. 5, a vial 30 is provided having a cap 28 adapted for compression fit within vial 30. Alternatively, a screw-type cap may be utilized. Again, as with the structure of FIG. 4, vial 30 may or may not be provided with an extraction fluid 32 initially, but an extraction fluid may be introduced into vial 30 after a sample has been collected on absorbent collector 16. In the apparatus of FIG. 5, shaft 14 of collection head 12 is provided with a bayonet mount structure 34 which allows collection head 12 to be removably attached to cap 28 by bayonet mount receiving structure 36 shown in phantom lines in cap 28 of FIG. 5. The bayonet mount structure permits 36 collection head 12 to be secured to cap 28 during the collection of a sample in the field and permits collection head 12 to be secured to cap 28 during the initial extraction of a specimen 32 from absorbent collector 16. However, once the extraction of sample from absorbent collector 16 into extraction fluid 32 has taken place, collection head 12 can be removed from cap 28 to allow the centrifugation process to take place without collection head 12 being present in vial 30 or extending into extraction fluid 32 during the centrifugation process. As previously stated, it is desirable to avoid having an absorbent collector 16 within extraction fluid 32 as the structure of an absorbent can mechanically capture within its structural matrix a portion of any sample 32 which is on absorbent collector 16.

Referring now to FIG. 7, a typical assay holder box 40 is shown in which vials 30 of the type shown in FIGS. 4 and 5 and 3 are inserted for analysis. It is to be appreciated that once the specimen has been extracted from absorbent collector 16 into the extraction fluid 32 of vial 30, that the vials can be placed in the typical assay box 40 normally used in laboratories, and therefore, the present apparatus and method of using the apparatus is adapted to conventional structured laboratory assays of multiple samples.

Figure 8:
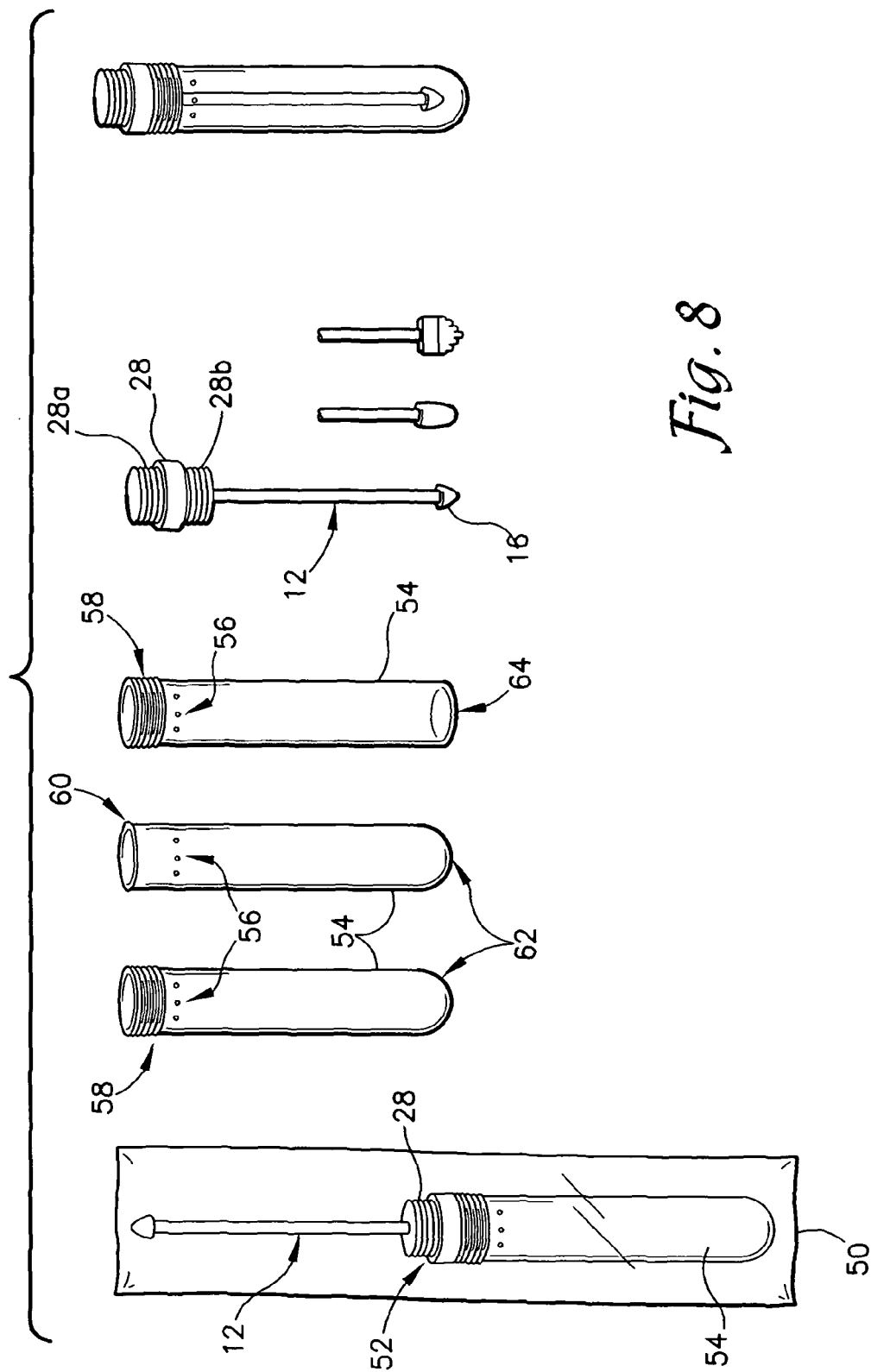
FIG. 8 shows a perspective view of an alternate embodiment of an evidence collection and storage device.

Referring now to FIG. 8, an alternative embodiment of the present collection device will be described. In FIG. 8, an embodiment of a touch evidence collection device is shown having an outer wrapper 50 containing collection device 52. Collecting device 52 is pre-prepared to allow obtaining a specimen by the user. The user can simply open package or container 50 and grasp collector 52 by vial 54 which, in this configuration of the apparatus shown in FIG. 8, operates as a handle and transport tube. Extending from vial or tube 54, which is acting as a handle, is collection head 12 which is attached to a cap 28. Cap 28 in this initial configuration of the device shown in FIG. 8 is inserted into vial or tube 54 to take advantage of the vial or tube 54 as a handle. The configuration of collection head 12 is shown wherein vial cap 28 is provided with a neck portion 28a, 28b which function to allow insertion of collection head 12 into tube or vial 54 as shown in FIG. 8 whereby tube or vial 54 is able to act as a handle for manipulating collection head 12. After a contact evidence sample is collected on absorbent collector 16 of collector head 12, the collector head 12 may be re-inserted into vial or tube 54 in reverse as is shown in FIG. 8. In this configuration, collection head 12 has been inserted into tube or vial 54, and the rim 28b is used to secure the collection head 12 into tube or vial 54 either by frictional fit between rim 28b and vial 54 or by the use of threads as is shown.

Further referring to FIG. 8, various configurations of vial 54 are shown. It will be appreciated that each of vials contain ventilation holes 56 which allow any moisture that is collected on absorbent collector 16 to exit vial 54 and allow absorbent collector 16 to dry while the specimen resides in absorbent collector 16 while collection head 12 is within any of such vials. The vials are provided with either a round bottom 62 or a flat bottom 64. It will be appreciated that the flat bottom 64 is convenient for standing the vial on a surface, while round bottom 62 is more convenient if the tube is intended to be centrifuged. As previously discussed, the vial may be equipped with threads 58 or simply a rim 60.

Figure 9:
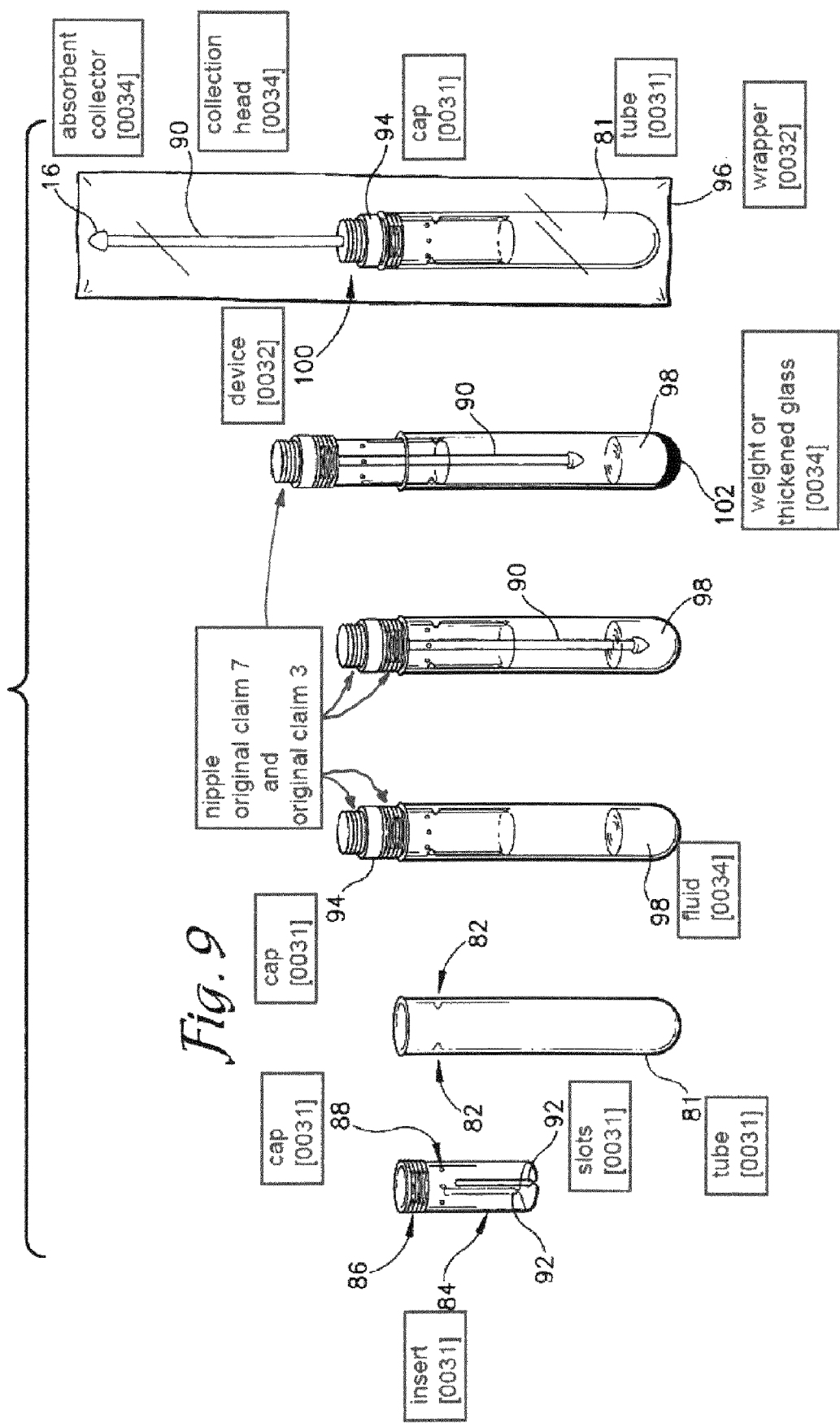
FIG. 9 shows a perspective view of an alternate embodiment of an evidence collection and storage device
Figure 10:
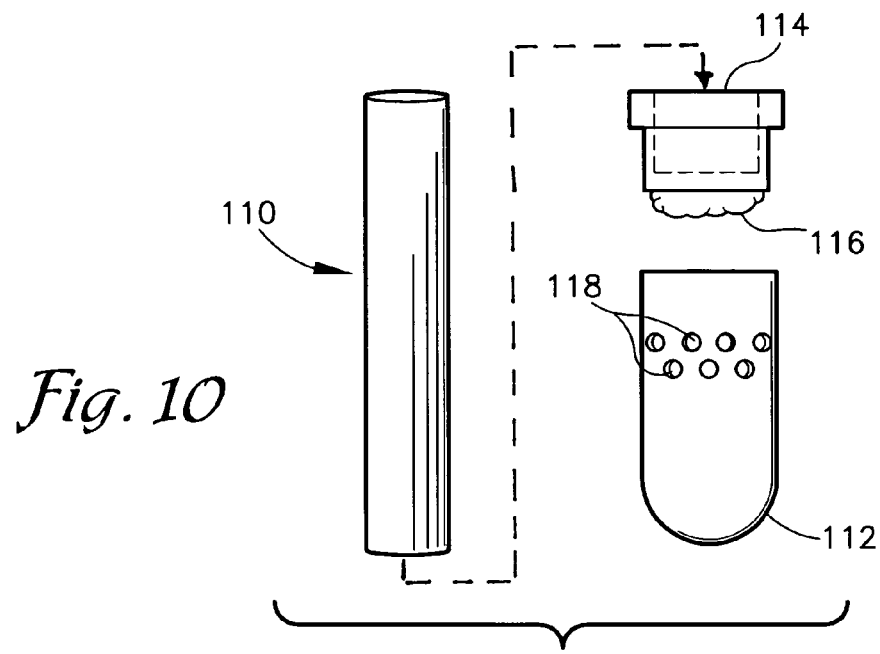
FIG. 10 shows an exploded view of an embodiment of an evidence collection and storage device

Referring now to FIG. 9, the system and apparatus is provided which allows for collection of a touch evidence specimen followed by the extraction of the specimen from the absorbent into an extraction solvent followed by centrifugation of the solvent during which the collection head and absorbent are separated from the extraction solvent as a result of the force of centrifugation all within the same apparatus.

Referring to FIG. 9, a tube or vial 81 is shown which is provided with indents 82 on opposed side wall portions of tube 81. Tube 81 may either be a rimmed tube as is shown in FIG. 9, or in an alternate embodiment, the tube could be provided with a threaded opening. Insert 84 is shown which fits within tube 81. Insert 84 is provided with a threaded rim 86 and voids 88 which allow for air migration in and out of insert 84 as well as tube 81. Voids 88 serve to vent tube 81 and allow for the evaporation of moisture so a sample placed on collection head 90 may dry while it is in vial 81. Still referring to FIG. 9, the interrelationship of tube 81 and insert 84 will be described. Insert 84 is intended to fit within tube 81 with indents 82 of tube 81 being registerable within slots 92 of insert 84. As is shown in FIG. 9, slots 92 are opposed and will align with indents 82 on tube 81 such that insert 84 is slidably mounted within tube 81 as is shown. The utility of the slidable mounting will be described hereinafter. Once insert 84 is placed within tube 81, the threads 86 on insert 84 may be used to seal the tube by attaching a threaded cap 94 to insert 84.

Further referring to FIG. 9, the contact evidence collection device 100 is shown prior to use in a wrapper 96 which excludes contamination from the entirety of device 100 which is packaged therein. When a user is ready to collect a contact evidence sample, wrapper 96 is opened and device 100 is extracted from the wrapper. Collection head 90 is ready for use as it has been inserted into tube 81 prior to the sealing of package 96 to allow tube 81 to act as a handle during the collection process. As has been previously described, the user will grasp the exterior of tube 81 using it as a handle to allow absorbent collector 16 of collection head 12 to contact the specimen for which collection is intended.

After a sample has been collected on absorbent collector 16, the user will grasp tube 81 and cap 94 and remove collection head 90 from tube 81 and invert collection head 90 and cap 94 and insert the absorbent collector 16 into tube 81 and reseal the tube 81 with cap 94 as shown. It will be appreciated by those skilled in the art that at this point, tube 81 may contain an extraction fluid 98 or the tube may be empty depending on the intended use of the sample and device 100. If the tube 81 does not contain an extraction fluid 98 but is intended simply to act as a storage means or a transport container for the specimen which has been collected on absorbent collector 16, tube 81 which is now in the configuration shown in FIG. 9, but without fluid 98 therein, may be stored or placed in a shipping package for shipment to a laboratory. If, however, the specimen collected on absorbent collector 16 is a wet specimen, and it is desired to allow air to circulate so the specimen may dry, the apparatus of FIG. 9 may be configured as is shown in FIG. 9, in which insert 84 is withdrawn slightly from tube 81 to allow increased air circulation in and out of tube 81 to permit specimen drying. It will be appreciated that in such an instance that fluid 98 will be absent from the tube.

The utility of this apparatus is employed to greatest effect when a liquid 98 is added into tube 81 for extraction of a sample from absorbent collector 16 and which sample previously has been obtained while absorbent collector 16 was employed as a contact evidence collection device 100. In this circumstance, after a specimen has been collected on absorbent collector 16, collection head 90, attached to cap 94 is removed from tube 81 which has been serving as a handle for the contact evidence collection, and collection head 90 is inserted into either a new vial 81 containing a fluid 98 or a fluid 98 is added into the original vial 81 and collection head 90 inserted into the fluid as is shown in FIG. 9. In the configuration of FIG. 9 with extraction fluid 98 added to tube 81, the contact evidence specimen which has been collected on absorbent collector 16 may be extracted by fluid 98 into fluid 98. After a sufficient period of extraction, it is often desired to centrifuge the extraction fluid 98 to remove solids that are in suspension in fluid 98. During such a centrifugation, it is desirable that absorbent collector 16 not be in contact with the fluid 98 as this has a tendency to trap amounts of specimen within the physical structure of absorbent collector 16. The apparatus of FIG. 9 is usefully employed in such a centrifugation operation by placing tube 98 into a centrifuge head which will grasp cap 94 leaving tube 81 and insert 84 free for relative movement. Once the centrifuge has started, the centrifugal force causes tube 81 to slide downwardly along opposed slits 92 thereby lowering tube 81 with respect absorbent collector 16 on collection head 90 and removing absorbent collector 16 from contact with solution 98 during the centrifugation process. Once centrifugation is complete, tube 81 may be removed from the centrifuge and subsequent analysis of extraction fluid 98 commenced. To assist the movement of tube 81 away from insert 84 during centrifugation, additional weight may be added to tube 81 by providing a thickened glass bottom 102 to tube 81 or by adding a weight to the bottom of tube 81.

Referring now to FIGS. 10 through 14, an alternate apparatus will be described for collection of touch evidence. The apparatus is comprised of a support stick 110 and a vented vial 112 having a cap 114 insertable in vial 112. Cap 114 has a collection absorbent 116 inserted into the base or attached to the base of cap 114. Vial 112 is provided with voids 118 which allow the passage of air in and out of vial 112 to allow drying of a sample contained therein.

Figure 11A:
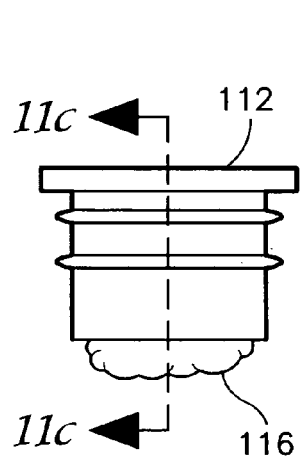
FIG. 11a shows an elevation view of the cap to an embodiment of an evidence collection and storage device
Figure 11B:
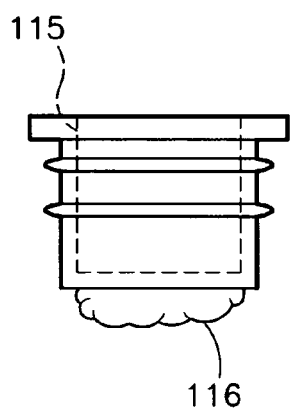
FIG. 11b shows an elevation view of the cap to an embodiment of an evidence collection and storage device showing a void for insertion of the support rod handle.
Figure 11C:
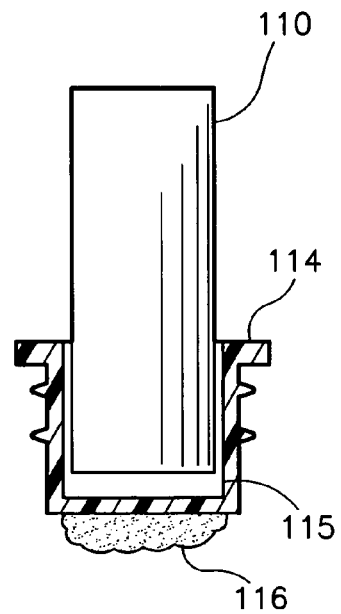
FIG. 11c shows an elevation view of the cap to an embodiment of an evidence collection and storage device showing insertion of the support rod handle.
Figure 12A:
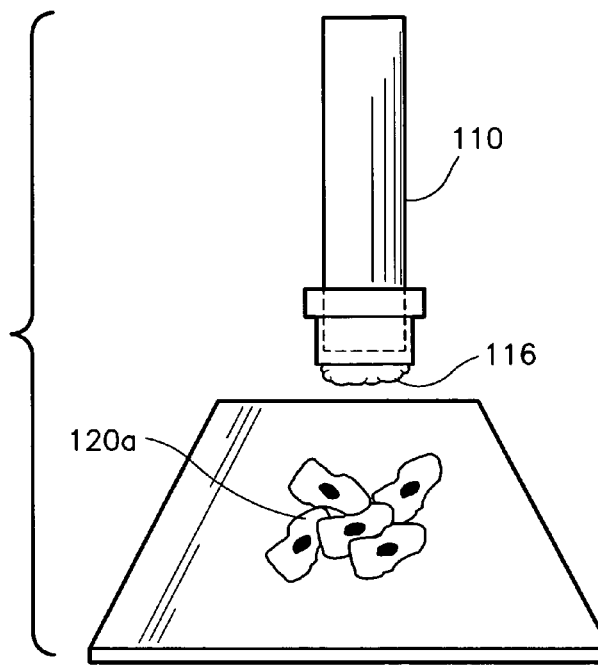
FIG. 12a shows a perspective view of an embodiment of an evidence collection and storage device.
Figure 12B:
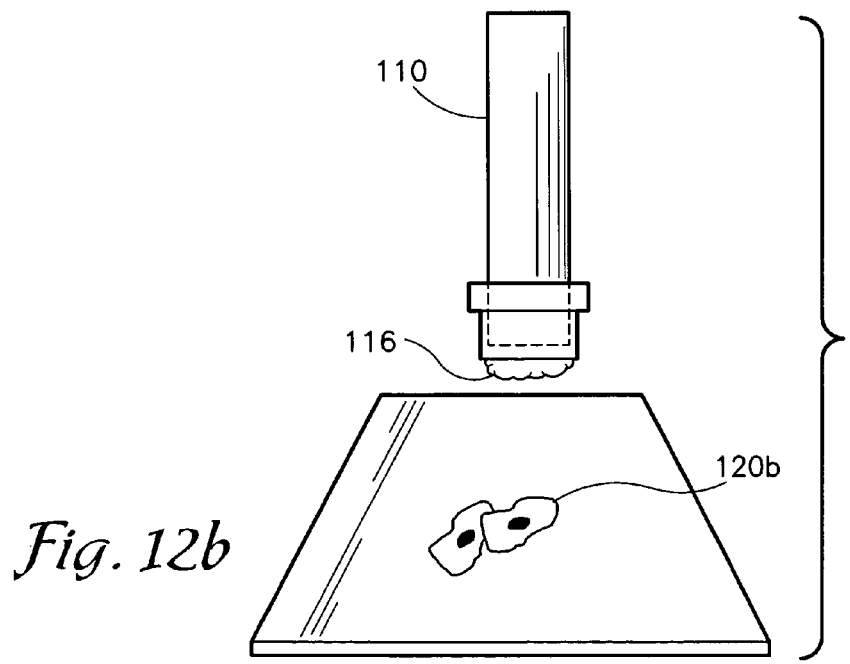
FIG. 12b shows a perspective view of an embodiment of an evidence collection and storage device noting specimen collection.
Figure 13:
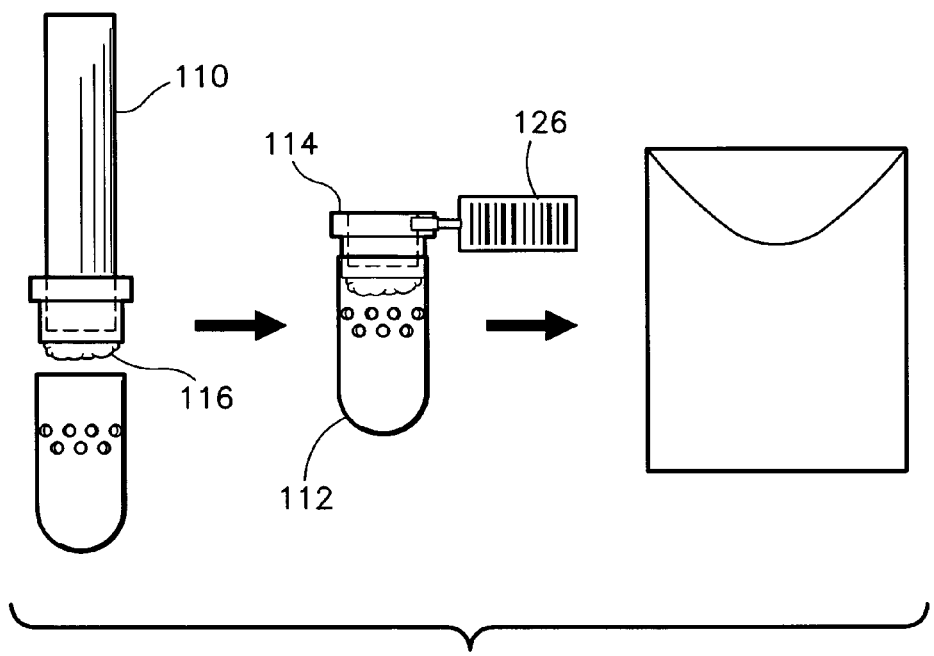
FIG. 13 shows an embodiment of an evidence collection and storage device.

Referring now to FIG. 11c support stick 110 is shown inserted into cap 114. This is achieved by a depression 115 that is created within cap 114 which is sized to receive support stick 110. In this manner, support stick 110 acts as a handle for manipulating cap 114 and collection absorbent 116 which is attached to cap 114. In FIG. 12, the collection device comprised of cap 114 and absorbent 116 with support stick 110 inserted into cap 114 is utilized to collect either a wet or dry contact evidence sample. This is accomplished by a user holding the device by handle 110 and contacting the absorbent 116 with the specimen 120a, 120b. Once the specimen 120a, 120b has been collected on absorbent 116, the user, still grasping handle 110, uses handle 110 to insert cap 114 into vial 112 (FIG. 13). Cap 114 may be frictionally captured within vial 112 or threads may be added to cap 114 and vial 112 to achieve closure in a threaded manner. Once cap 114 is inserted vial 112, support stick 110 may be separated from the cap and vial unit as shown in FIG. 13. When support stick 110 has been separated, the user can grasp vial 112 and transport vial 112 to a laboratory in any convenient method possible such as, for example, transport envelop shown in FIG. 13.

Figure 14:
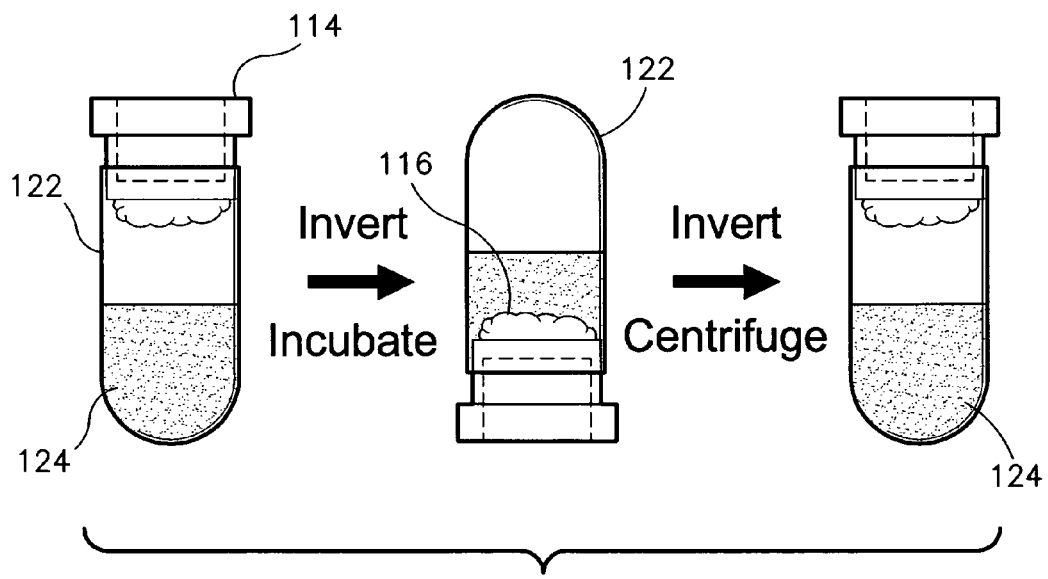
FIG. 14 shows a vile used in conjunction with the evidence collection and storage device to facilitate the evidence extraction process.

Referring now to FIG. 14, after vial 112 with cap 114 thereon has been transported to the lab; the extraction process may take place by transferring cap 114 onto a second vial 122 which does not have voids 118 therein allowing the passage of air. An extraction fluid or lysis buffer 124 is provided in vial 122 and while vial 122 with cap 114 thereon is inverted to bring the buffer into contact with absorbent 116 having a collected sample thereon. The sample collected on absorbent 116 is extracted into lysis buffer 124 after a sufficient amount of extraction time, the tube 122 is placed into a centrifuge, and the lysate 124 is removed from contact with absorbent 116.

It will be appreciated that cap 114 is provided with identification indicia such as bar code 126 (as shown in FIG. 13). Bar code 126 is applied directly to cap 114, and multiple copies of bar code 126 may be applied around the circumference of cap 114 so that as the specimen is ultimately extracted from absorbent 116 and into a buffer 124, the bar code 126 associated with cap 114 may be transferred onto a subsequent vial 122 to ensure the chain of custody during the handling of the sample.

Certain changes may be made in embodying the above invention, and in the construction thereof, without departing from the spirit and scope of the invention. It is intended that all matter contained in the above description and shown in the accompanying drawings shall be interpreted as illustrative and not meant in a limiting sense.

Having now described the features, discoveries and principles of the invention, the manner in which the touch evidence collection device is constructed and used, the characteristics of the construction, and advantageous, new and useful results obtained; the new and useful structures, devices, elements, arrangements, parts and combinations, are set forth in the appended claims.

It is also to be understood that the following claims are intended to cover all of the generic and specific features of the invention herein described, and all statements of the scope of the invention which, as a matter of language, might be said to fall there between.

We claim:

1. A collection tube and swab device comprising:
a tube having a continuous sidewall and first and second ends said first end being closed and said second end being open,
a generally tube-shaped insert coaxially mounted within said tube second end, said insert having,
a generally continuous sidewall and open first and second ends,
at least one slot on said insert partially extending along the length of said insert,
at least one void in said insert sidewall allowing the passage of gas therethrough,
at least one indent extending inwardly from said tube sidewall for slideable engagement with said slot, said indent and slot configured for movement of said insert between a first position in which said insert is generally within said tube and a second position in which said insert is partially extended from said tube to expose said void to permit passage of gas in and out of said tube,
a cap removable from said insert said cap having a central body having a first side and a second side each of said sides having a nipple portion extending therefrom, each of said nipples being insertable within said insert to seal close the open end of said insert that is seated in said tube open end, and
a collection head comprising a shaft having first and second ends, an absorbent collector mounted on said shaft first end and said shaft second end being connected to one of said cap nipples to permit insertion of the other cap nipple within said insert to configure said insert and tube as a handle during evidence collection, and whereby said cap nipple having said shaft second end connected thereto provides securing of said collector within said insert for protected storage of said absorbent collector within said tube upon insertion of said shaft second end and said collector into said tube.

2. The device as claimed in claim 1 wherein said nipples extending from said first and second sides are threaded and said insert is threaded for screw connection with said nipples.

3. The device as claimed in claim 1 wherein said tube is provided with additional weight on the tube closed first end.

4. The device as claimed in claim 1 wherein the distance of movement of said insert from said first position to said second position is sufficient to remove said absorbent collector from contact with a solution in said tube during a centrifugation process.

* * * * *

UNITED STATES PATENT AND TRADEMARK OFFICE
CERTIFICATE OF CORRECTION

PATENT NO. : 8,075,850 B2
APPLICATION NO. : 11/653116
DATED : December 13, 2011
INVENTOR(S) : Jangbir S. Sangha and Todd Bille Page 1 of 1

It is certified that error appears in the above-identified patent and that said Letters Patent is hereby corrected as shown below:

In claim 1, column 8, line 29, the word "seal" should be deleted.

Signed and Sealed this
Twenty-eighth Day of February, 2012

David J. Kappos
*Director of the United States Patent and Trademark Office*